(12) United States Patent
Ortiz

(10) Patent No.: US 6,662,804 B2
(45) Date of Patent: Dec. 16, 2003

(54) TRACHEOSTOMY TUBE WITH CUFF ON INNER CANNULA

(76) Inventor: Antonio Ortiz, 2659 Kingsbridge Terrace, Bronx, NY (US) 10463

( * ) Notice: Subject to any disclaimer, the term of this patent is extended or adjusted under 35 U.S.C. 154(b) by 43 days.

(21) Appl. No.: 10/045,053

(22) Filed: Jan. 15, 2002

(65) Prior Publication Data

US 2003/0084905 A1 May 8, 2003

Related U.S. Application Data

(60) Provisional application No. 60/330,924, filed on Nov. 2, 2001.

(51) Int. Cl.$^7$ ............................................. A61M 16/00
(52) U.S. Cl. .............................. 128/207.14; 128/207.15
(58) Field of Search ...................... 128/207.14, 207.15, 128/207.18, 200.26, 912, DIG. 26; 604/264, 265

(56) References Cited

U.S. PATENT DOCUMENTS

| | | | | |
|---|---|---|---|---|
| 2,765,792 A | | 10/1956 | Nichols ...................... 128/351 |
| 2,786,469 A | | 3/1957 | Cohen ......................... 128/351 |
| 3,088,466 A | | 5/1963 | Nichols ...................... 128/351 |
| 3,461,877 A | | 8/1969 | Morch ......................... 128/351 |
| 3,504,676 A | | 4/1970 | Lomholt ..................... 128/351 |
| 3,659,612 A | | 5/1972 | Shiley et al. ............... 128/351 |
| 4,009,720 A | | 3/1977 | Crandall et al. ............ 128/351 |
| 4,033,353 A | | 7/1977 | La Rosa .................... 128/351 |
| 4,037,605 A | * | 7/1977 | Firth ...................... 128/207.15 |
| 4,150,676 A | | 4/1979 | Jackson ....................... 128/351 |
| 4,235,229 A | * | 11/1980 | Ranford et al. ......... 128/207.17 |
| 4,246,897 A | | 1/1981 | Muto ...................... 128/207.15 |
| 4,315,505 A | * | 2/1982 | Crandall et al. ........ 128/200.26 |
| 4,331,144 A | | 5/1982 | Wapner .................. 128/207.15 |
| 4,817,598 A | | 4/1989 | LaBombard ............ 128/207.14 |
| 4,852,565 A | * | 8/1989 | Eisele .................... 128/207.14 |
| 5,052,386 A | * | 10/1991 | Fischer, Jr. ............. 128/207.15 |
| 5,056,515 A | * | 10/1991 | Abel ...................... 128/207.15 |
| 5,067,496 A | * | 11/1991 | Eisele .................... 128/207.15 |
| 5,217,008 A | | 6/1993 | Lindholm ............... 128/207.14 |
| 5,222,487 A | | 6/1993 | Carr et al. ............. 128/200.26 |
| 5,222,491 A | | 6/1993 | Thomas .................. 128/205.13 |
| 5,322,062 A | * | 6/1994 | Servas .................... 128/207.14 |
| 5,390,669 A | * | 2/1995 | Stuart et al. ........... 128/207.14 |
| 5,458,139 A | * | 10/1995 | Pearl ..................... 128/207.14 |
| 5,515,844 A | * | 5/1996 | Christopher ........... 128/200.26 |
| 5,762,638 A | * | 6/1998 | Shikani et al. .............. 604/265 |
| 5,778,877 A | | 7/1998 | Stuart .................... 128/207.17 |
| 5,840,091 A | * | 11/1998 | Strong ........................ 55/385.1 |
| 5,957,978 A | * | 9/1999 | Blom ............................. 623/9 |

(List continued on next page.)

OTHER PUBLICATIONS

McPherson, Respiratory Care Equipment, Ed. 5, 1995, pp 118–127.

Scanlan et al, Egan's Fundamentals of Respiratory Care, Ed. 6, 1995, pp. 540–580.

*Primary Examiner*—Weilun Lo
*Assistant Examiner*—Teena Mitchell

(57) ABSTRACT

BACKGROUND: Tracheotomy is used to assist patients who require mechanical ventilation. Tracheostomy is a common surgical procedure for intensive care patients. The goals of tracheotomy are to bypass the upper airway, facilitate removal of tracheobronchial secretions, prevent aspiration of gastric contents, and to control the airway for prolonged mechanical ventilation. METHOD: The hypothesis to improve the design of the tracheostomy tube, making it easier to use and eliminating most of the disadvantages found in prior tracheostomy tubes. RESULTS: This device is an improved tracheostomy tube designed with the balloon cuff (18), guide balloon (26), balloon connector (32) and guide balloon valve (24) located on the inner cannula (12). The major improvement in this tracheostomy tube is that the removal of the outer cannula will not be necessary when the balloon cuff is damaged, since replacing the inner cuffed cannula corrects the problem.

3 Claims, 4 Drawing Sheets

U.S. PATENT DOCUMENTS

| | | | | |
|---|---|---|---|---|
| 5,983,895 A | | 11/1999 | Turner | 128/207.14 |
| 6,019,753 A | * | 2/2000 | Pagan | 604/523 |
| 6,105,577 A | * | 8/2000 | Varner | 128/207.17 |
| 6,135,110 A | * | 10/2000 | Roy | 128/207.15 |
| 6,135,111 A | * | 10/2000 | Mongeon | 128/207.15 |
| 6,284,179 B1 | * | 9/2001 | Deily et al. | 264/254 |
| 6,588,426 B2 | * | 7/2003 | Linderoth | 128/207.14 |
| 2002/0078962 A1 | * | 6/2002 | Nash et al. | 128/207.15 |

* cited by examiner

TRACHEOSTOMY TUBE WITH CUFF ON INNER CANNULA

CROSS-REFERENCE TO RELATED APPLICATION

This application claims the benefit of Provisional Patent Application Ser. No. 60/330,924 filed Nov. 2, 2001.

BACKGROUND

1. Field of Invention

This invention relates to tracheostomy tubes having a curved shape, and oval or round cannulas used in the surgical instruments and accessories field for patients that have respiratory failure, respiratory tract obstructions, restrictions, lung injury and or disease.

2. Description of Prior Art

Tracheotomy has been used to assist patients who require mechanical ventilation. Tracheostomy is a common surgical procedure for intensive care patients. The goals of tracheotomy are to bypass the upper airway, facilitate removal of tracheobronchial secretions, prevent aspiration of gastric contents, and to control the airway for prolonged mechanical ventilation. Tracheostomy tubes provide life-sustaining support for patients who have obstructions, restrictions, injuries and or disease of the airway or lungs. A Physician surgically inserts a tracheostomy tube into a patient's incision or stoma to bypass the upper airway, between the vocal cords and the bifurcation of the carina. Originally, tracheostomy tubes were made of silver such as the Jackson Tracheostomy tubes that are still produced (McPherson SP: Respiratory Care Equipment, ed 5, pp. 118–127, St. Louis, 1995, Mosby). However, metal tracheostomy tubes are difficult to clean and tarnish with time. Metal tracheostomy tubes are also expensive to make and deform or bend out of shape. Also, certain metals are irritating to the patient's tissues. Therefore, natural rubber was used for manufacturing endotracheal tubes of the Jackson type, to U.S. Pat. No. 4,150,676 but not limited to this patent, later giving way to various types of plastics like Polyvinyl chloride (PVC). A thin surgical rubber or silicone sold under the trademark, SILASTIC of Dow Corning Corp., is also used.

Current tracheostomy tubes now come in pairs or sets, where an inner cannula is fitted into an outer cannula. There are several devices, which contain a means of locking or connecting the inner cannula to the outer cannula and the cannulas to the ventilation system. These include, but are not limited to U.S. Pat. No. 3,659,612 to Shiley et al., U.S. Pat. No. 4,009,720 to Crandall, et al., and U.S. Pat. No. 3,088,466 to Nichols. Tracheostomy tubes may remain in the airway for long periods of time, and require frequent cleaning of the inner cannula. Unfortunately, wear and tear causes problems with the means of connecting the cannulas to each other, and the ventilator circuit. The inner cannula is also manufactured separately from the set, since it tends to wear out faster than the outer cannula.

Another problem associated with tracheostomy tubes is with the balloon cuff. The first cuffs were elastic, balloon like structures that laid flat against the tube at rest. These elastic balloon cuffs had to have pressure applied from within, to actively stretch the cuff until it pressed against the airway to make a seal. This type of cuff is referred to as a low-residual-volume, high-pressure cuff. Because cuffs of this type tend to cause sufficient pressure on the respiratory tract mucosa of the trachea to stop capillary blood flow, maneuvers such as the minimal leak technique are use. In this technique a slight leak during inhalation is allowed around the cuff, for patients receiving long-term mechanically supported ventilation. When just enough volume is used to occlude the airway, the technique is referred to as the minimal occluding volume. Periodic deflation of the cuff every hour for 5 minutes has also been used, although the adequacy of this technique has been questioned. These methods have been devise to try to minimize the potential of tracheal wall dilation, and mucosal necrosis with long-term use of cuffed tubes (Scanlan C L., et al: Egan's Fundamentals of Respiratory Care, pp. 540–580, ed 6. St. Louis, 1995, Mosby).

Reducing the potential of necrosis also prompted the development of other types of cuff designs with high-residual-volume and low pressure. These cuffs are larger that high-pressure cuffs and are actively deflated for insertion, then partially inflated with enough air to obtain a seal against the tracheal wall. Low-volume, high-pressure cuffs may exert less than 25 mmHg. Examples of tubes incorporating the newer low-pressure designs are sold under the trademark SOFT-CUF by Forreger Company, Inc., and the trademark SOFT-SEAL by Portex Limited Company. Shiley et al., also makes a tube with a cuff that has a relatively large residual volume. Shiley et al's cuff is cylindrical in shape, is made of comparatively rigid material, and is also said to inflate evenly. Tracheostomy tubes disclosed in U.S. Pat. No. 3,659,612 to Shiley et al., and U.S. Pat. No. 4,009,720 to Crandall shows a similar cuff mechanism including a pilot tube attached to a balloon, which is inserted within the airway located on the outer cannula. There are other examples of balloon cuffs and regulating valves, etc., and the above should be considered as examples or illustrative and should not be considered limiting to the particular forms shown.

When the tracheostomy tube is placed into the stoma, the balloon cuff is placed between the vocal cords and the carina. Once the cuff gets worn or has too much air added into it, the cuff is damaged and must be replaced. This entails removal of the outer cannula, in order to replace the balloon cuff. Irritation, pain and or bleeding can also occur to the patient's stoma site during the cuff replacement procedure. The current procedure for balloon cuff replacement also entails the removal of the retaining strap that is attached to the flange on the outer cannula. This cord holds the tracheostomy tubes in place around the patients' neck. One type of strap or cord for supporting tracheostomy tubes is described in U.S. Pat. No. 4,331,144 to Wapner, and there are others as well.

La Rosa in U.S. Pat. No. 4,033,353 describes but is not limited to a neck flange made of a flexible material to which a tracheostomy tube is mounted by flexible portions thereof Flanges and straps irritate the patient's neck, causing discomfort, redness and rashes to occur to the surrounding outer neck area.

Current tracheostomy tubes having long outer cannulas can cause a condition where the trachea is irritated, and a hole (tracheoesophageal fistula) forms in the posterior wall adjoining the esophagus. Other tracheal lesions that occur are tracheal granulomas, tracheomalacia, and tracheal stenosis. Tracheal granulomas usually form in the trachea near the tracheal tube tip. They are probably related to tube movement. Another site of granulomas development is the tracheal stoma itself This may be due to a foreign body reaction. Tracheomalacia and tracheal stenosis occur either separately or together. Tracheomalacia is the softening of the cartilaginous rings, which causes collapse of the trachea during inspiration. Processes similar to those causing mucosal ulceration may lead to debridement of the epithelium, and exposure and necrosis of the tracheal rings. The extent of tracheomalacia depends on the degree of damage to the cartilage. In patients with tracheostomy tubes, stenosis may occur either at the cuff site or at the tip of the tube. Stenosis at the stoma site is more common. Typically, stenosis at the stoma occurs when the sides of the incision pull together during healing. Usually the posterior wall of the trachea is unaffected. Stenosis at the stoma site may be caused by too large a stoma, infection of the stoma, movement of the tube, or frequent tube changes (McPherson S P: Respiratory Care Equipment, ed 5, pp. 118–127, St. Louis, 1995, Mosby).

Artificial airways are fundamentally simple devices designed to provide the patient with a patent airway, reduce the work of breathing, enhance clearance of pulmonary secretions, and provide a route for the administration of ventilatory assistance or control. It is an important requirement that tracheostomy tubes provide an air supply to the patient, while minimizing their discomfort. Practitioners must use the proper equipment and procedure with sound techniques of airway management and maintenance, in order to minimize the possibility of serious complications to the patient's airway.

Objects and Advantages

From the description above, a number of objects and advantages of my tracheostomy tube become evident:

a) Accordingly, the main object and advantage in my tracheostomy tube is to provide an improved tracheostomy tube in which aforementioned disadvantages will be decreased.

b) Another object and advantage to my tracheostomy tube to improve the safety and reduce the possible chances for serious complications.

c) Still another object and advantage in my design is to prevent and or reduce tracheoesophageal fistulas from developing and or healing if already present.

d) It is also another object and advantage in my tracheostomy tube design to help seal and prevent secretions from accumulating between the outer and inner cannulas.

e) An additional object and advantage in my tracheostomy tube is that the outer and inner cannulas can be attached or mated for added security.

f) A further object and advantage in my tracheostomy tube is to make it lighter and stronger.

g) Yet another object and advantage in my tracheostomy tube is that the replaceable inner cannula design will make it easier to replace the balloon cuff.

h) A extra object and advantage in my tracheostomy tube is to provide the patient with a more comfortable tracheostomy tube.

i) It is a further object and advantage that my tracheostomy tube provides an easier replacement procedure for the health care practitioners, when removing the balloon cuff.

Further objects and advantages with my Tracheostomy tube will become apparent from a consideration of the drawings and ensuing description, which will reinforce and affirm my invention.

SUMMARY

In accordance with the present invention an improved tracheostomy tube comprises a balloon cuff, balloon connector, guide balloon valve, and guide balloon located on the inner cannula and inserted into a shorter uncuffed outer cannula. When the tracheostomy tube set is inserted in the tracheal stoma, the set will be held in place by means of a strap wrapped around the patient's neck and attached to eyelet's located on the outer cannula retainer.

DRAWINGS

Drawing Figures

REFERENCE NUMERALS IN DRAWINGS

| 10 | swivel locking adapter |
| 12 | inner cannula |
| 14 | outer cannula |
| 16 | outer cannula retainer |
| 18 | balloon cuff |
| 20 | guide balloon |
| 22 | open port |
| 24 | guide balloon valve |
| 26 | radio opaque marking |
| 28 | stoma insertion tool |
| 30 | swivel eyelet |
| 32 | balloon connector |
| 34 | outer cannula cover |
| 36 | inner cannula ring |
| 38 | outer cannula ring indentation |

DETAILED DESCRIPTION

Figure 1:
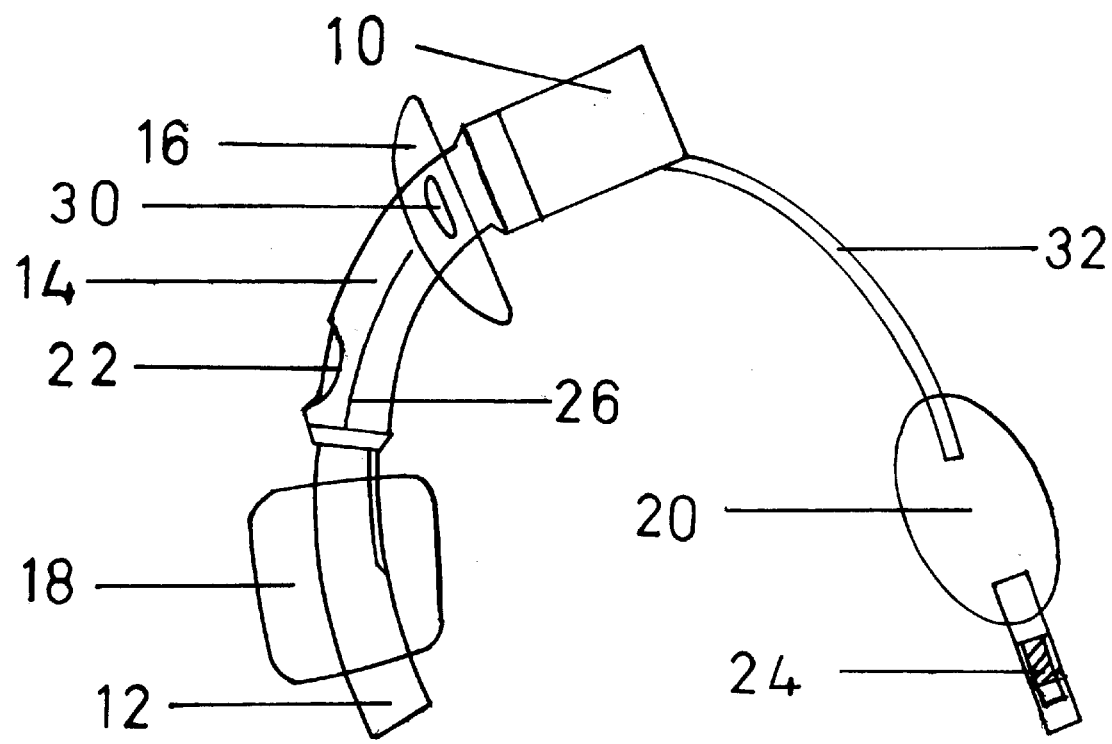
FIG. 1 is a right-side view of the tracheostomy tube set with the cuff located on the inner cannula, which has been inserted into the short outer cannula.

Description—FIG. 1—Preferred Embodiment

A preferred embodiment view taken from the users right side of the completely assembled tracheostomy set tube with a outer cannula 14 and a balloon cuff 18 located on a inner cannula 12 is illustrated in FIG. 1. The items are constructed of non-toxic plastic, silicone or synthetic materials in accordance with the invention. The upper portion of the inner cannula 12 has a swivel-locking adapter 10 made of a bonded plastic, for attaching the positive pressure ventilator circuit. The outer cannula 14 (FIG. 2) is made of polyvinyl chloride (PVC) and encloses the inner cannula 12, which can be made of a softer non-toxic plastic, rubber or silicone material. The outer cannula 14 has an outer cannula retainer 16 with a swivel attached to the main upper body of the outer cannula 14. This swivel is for the retainer cord or strap placed through the swivel eyelet 30, and tied around the patient's neck to maintain the outer cannula 14 tube in the proper anatomical position within the trachea.

Figure 2:
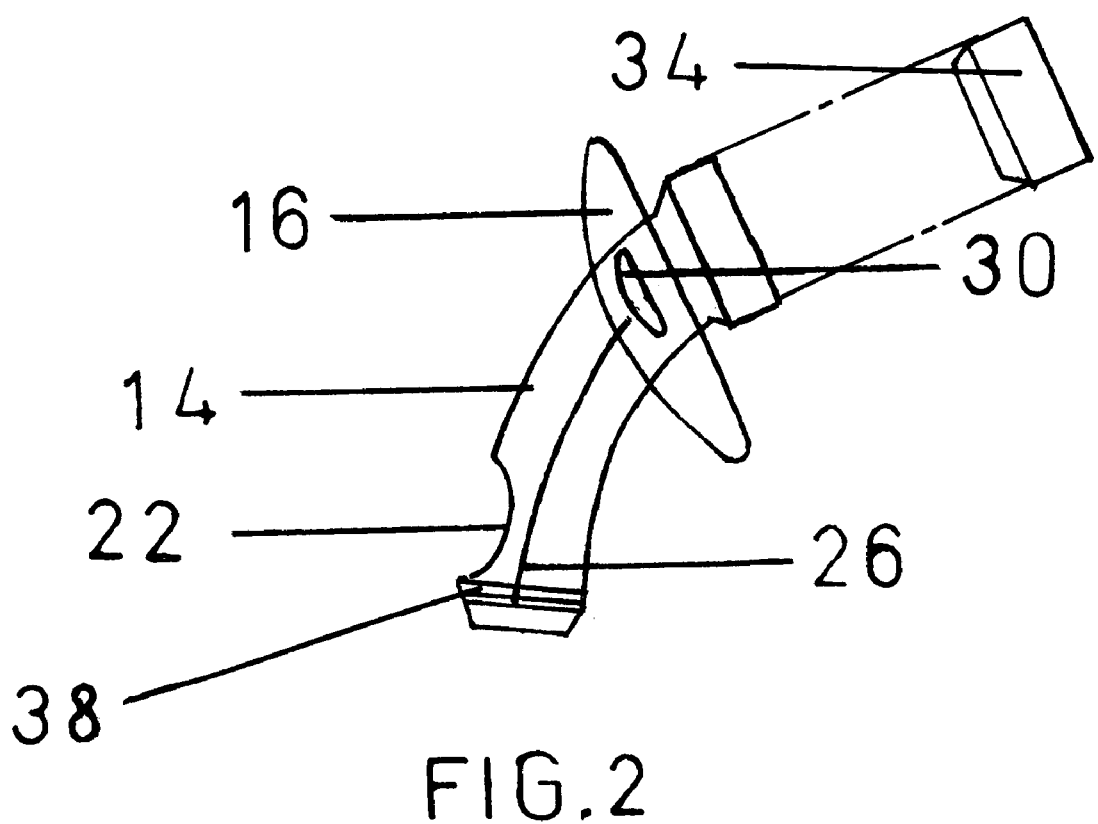
FIG. 2 is a right-side view of the tracheostomy tube's outer cannula, with the outer cannula cover.

FIG. 2—Additional Embodiment

Figure 3:
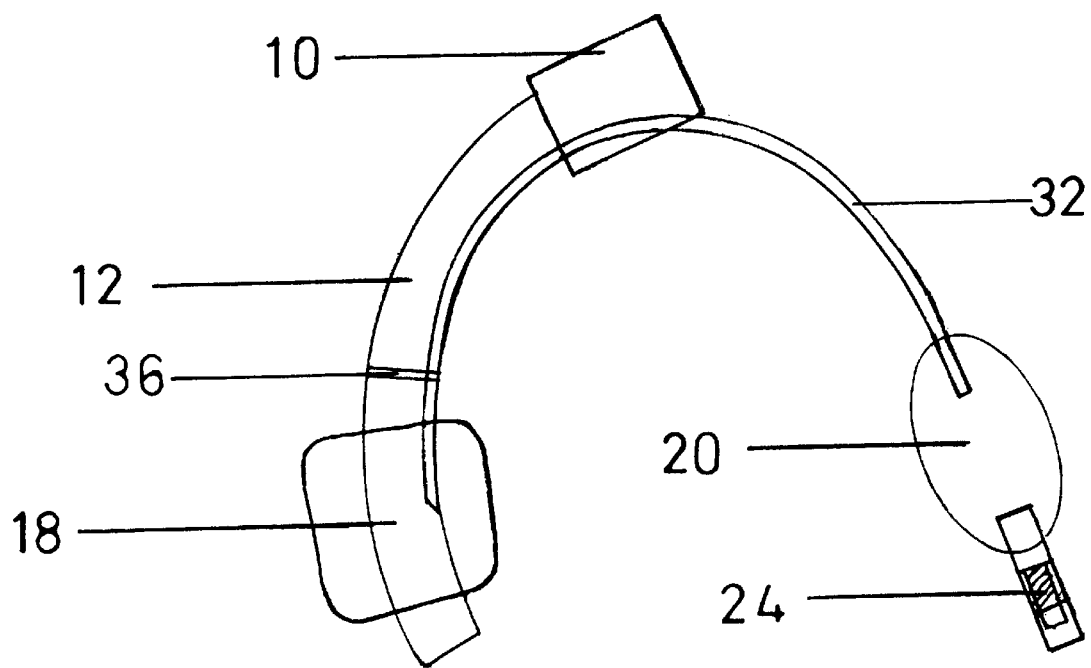
FIG. 3 is a right-side view of the tracheostomy tube's inner cannula, with the balloon cuff, balloon connector, guide balloon valve and guide balloon assemblies.

An additional embodiment view taken from the users right side of a outer cannula 14 which can be made of PVC, and a outer cannula cover 34 made of non-toxic silicone or rubber is presented in FIG. 2. The outer cannula 14 will have an open port 22 located on it, in order to provide weaning when the patient is not being provided with positive pressure ventilation through the cuffed inner cannula 12 (FIG. 3). An outer cannula cover 34, which will close the outer cannula 14 when inserted into it, will allow the patient to breath through their upper airway. Once the outer cannula cover 34 is in use, the patient will breathe through their nose and or mouth when weaning, then testing of the airway can be done. An open port 22 tube, is a cannulated tube that has an opening in the posterior wall of the outer cannula 14. Removal of the inner cannula 12 (FIG. 3) after deflation and removal of the balloon cuff 18 (FIG. 3) opens the open port 22. Removal of the outer cannula cover 34 allows access for suctioning the inner airway of excess secretions when necessary. When the need for mechanical or manual ventilation occurs, the outer cannula cover 34 can be removed and the inner cannula 12 can be inserted (FIG. 3). Then the balloon cuff 18 (FIG. 3) can be inflated, in order to seal the airway for positive pressure ventilation. The outer cannula ring indentation 38 will provide a notch, where the inner cannula ring 36 (FIG. 3) can attach and seal both cannulas from accumulation of secretions between them. The length of the outer cannula 14 can be manufactured in various sizes, so that the selected one fits within the specific airway properly. A radio opaque marking 26 is located on the outer cannula 14, in order to indicate the proper placement and size of the tube in the trachea, when verified via a lateral upper tracheal x-ray.

FIG. 3—Additional Embodiment

FIG. 3 is an additional embodiment illustration taken from the users right of a inner cannula 12. The inner cannula 12 has a balloon cuff 18 bonded on the lower portion, with a guide balloon 20, balloon connector 32, and a guide balloon valve 24 used to inflate it with air so that the pressure will not exceed 19–25 mmHg. The bonded parts that will consist of the guide balloon 20, balloon connector 32, guide balloon valve 24, and balloon cuff 18 will be made of a non-toxic synthetic and or plastic material. The balloon cuff 18 functions to seal the inner tracheal airway below the vocal cords and carina when properly inserted in the stoma and precisely positioned in the trachea and verified via a lateral upper tracheal x-ray. The balloon connector 32 attaches and connects the balloon cuff 18 with the guide balloon 20. Then when the guide balloon valve 24 is filled with 19–25 mmHg of air, the balloon cuff 18 will be inflated and seal the inner airway for positive pressure ventilation. The inner cannula 12 is longer that the outer cannula 14 (FIG. 2.). The external diameter of the inner cannula 12 is slightly smaller than the internal diameter of the outer cannula 14 (FIG. 2), so that the inner cannula 12 and balloon cuff 18 can be easily inserted into the outer cannula 14 (FIG. 2). Various sizes of outer and inner cannulas will be made for infants, adolescents, adults and geriatric patients. The inner cannula 12 will have a synthetic and or rubber ring or the inner cannula ring 36 bonded on the outer midway point, so that it can mate with the outer cannula ring 38 indentation within the inner diameter of the lower outer cannula 14 (FIG. 2). This ring on the inner cannula 12 exterior will prevent any secretions from traveling upward between the cannulas when they are mated. This ring will also prevent air leaks, and also provide a locking mechanism to secure both cannulas together. The thickness and or size of the inner cannula ring 36 will be just enough, so that it will easily clear the inner walls of the outer cannula 14 (FIG. 2) on insertion or removal along with the balloon cuff 18 assembly.

Figure 4:
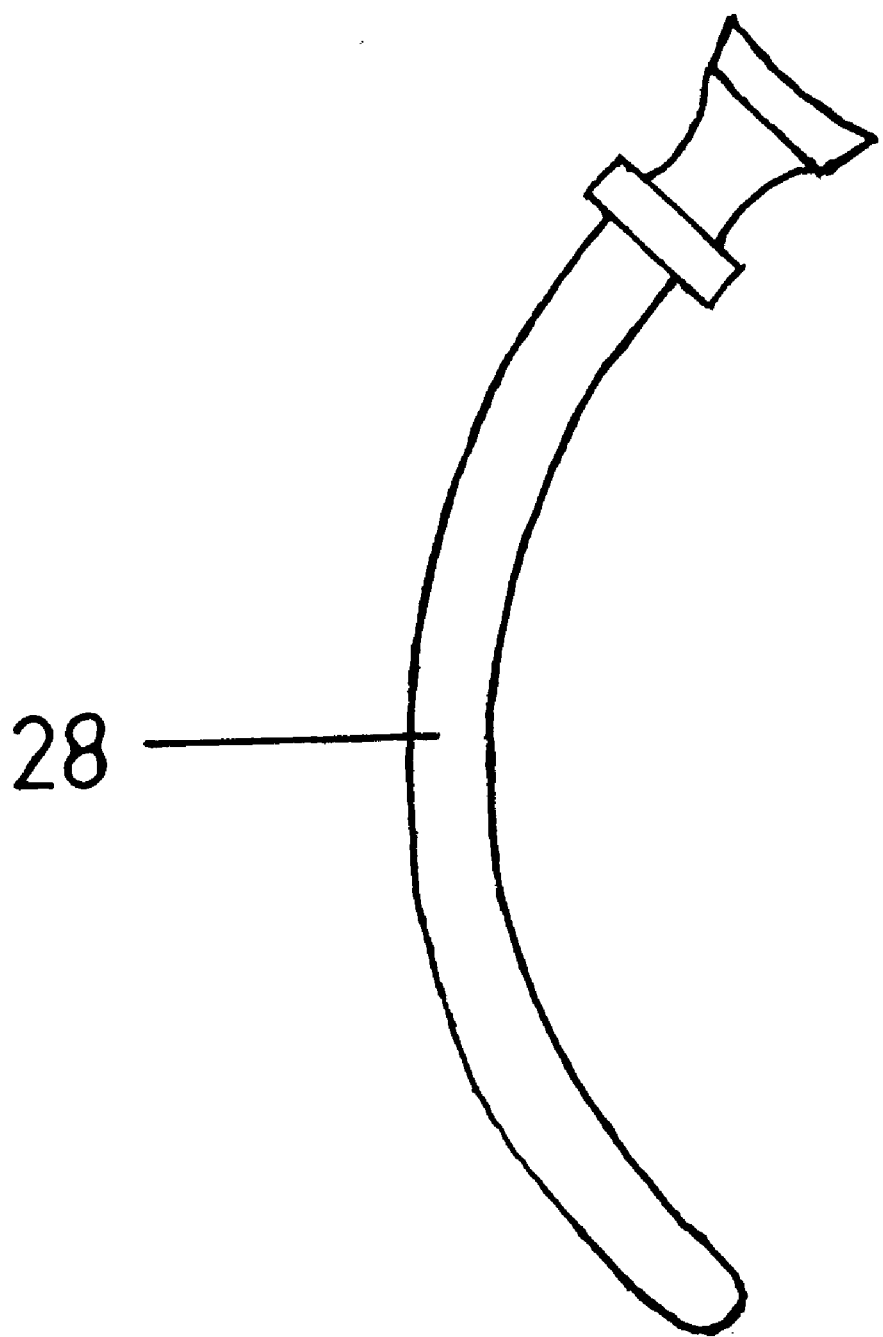
FIG. 4 is the right-side view of the stoma insertion tool used to help insert the outer cannula into the tracheal airway incision or stoma.

FIG. 4—Additional Embodiment

FIG. 4 is an additional embodiment view taken from the users right side of a stoma insertion tool 28 also made of PVC. A stoma insertion tool 28 is inserted into the outer cannula 14 (FIG. 2), in order to facilitate and guide the placement of the outer cannula 14 (FIG. 2) into the stoma.

Operation

In operation one uses the tracheostomy tube with a balloon cuff located on the inner cannula in a patient's trachea to overcome upper airway obstruction, restriction, trauma or due to diseased airways, lungs and or impaired gas exchange. Adequate gas exchange or the maintenance of the proper blood levels of PH, partial pressure of carbon dioxide (PCO2), Bicarbonate (HCO3) and Oxygen Saturation (O2Sat) or what is known in the medical field as acid-base balance, is not possible if a patients airway is not provided, even with normal lungs. The importance of an adequate airway is demonstrated in the sequencing of Cardio Pulmonary Resuscitation (CPR) procedures, when the airway is given first priority.

First and foremost, the balloon on the inner cannula must be leak tested, by inflating it with a syringe through the guide balloon valve and then immersing the inflated balloon cuff in sterile saline to observe for air leakage, after which the balloon once passing the leak test can be deflated for insertion into the outer cannula.

Secondly, after the appropriate medical safety measures are provided for the patient, the user can insert the outer cannula into the trachea through an incision, or stoma with the help of a guide device called a stoma insertion tool. The stoma insertion tool is temporarily placed into the outer cannula, in order to help guide the outer cannula into the stoma. A water-soluble lubricant must be applied to both the stoma insertion tool and outer cannula, prior to its insertion into the stoma. Examples of obturators or stoma guidance tools are described but not limited, for example in U.S. Pat. No. 4,246,897 to Muto, and in U.S. Pat. No. 5,222,487 to Carr et al. Once the outer cannula is in its proper position, the stoma guidance tool can be removed, and the inner cannula can be inserted and snapped into the outer cannula and secured in place by a locking mechanism. The inner-cuffed cannula must also have the water soluble lubricant applied to it and to its balloon as well, prior to its insertion into the uncuffed outer cannula. Then a syringe is attached to the guide balloon valve, so that the inner cannula cuff is filled with air, not to exceed 19–25 mmHg. Then a retaining strap can be attached to the outer cannula retainer through the swivel eyelet attached and located on the upper portion of the outer cannula, in order to maintain the tracheostomy tube set in the proper position. U.S. Pat. No. 4,033,353 to La Rosa describes but is not limited to a neck flange made of a flexible material to which a tracheostomy tube is mounted by flexible portions thereof In addition, for temporary ventilation whenever the need arises, an air-mask-bag-unit (AMBU) can also be attached to the tracheostomy tube swivel-locking adapter, as shown but not limited to in U.S. Pat. No. 5,222,491 to Thomas.

Finally, there will be occasions where the inner cannula or both the inner cannula and outer cannula must be removed due to weaning, upper airway assessment, an obstruction or damage to either or both of the cannulas, special tests or procedures and or when ventilation is terminated. Then a competently trained health care practitioner can remove the inner cannula or both cannulas, in order to replace either one and or both of them with another set or to terminate ventilation when necessary.

Conclusion, Ramifications and Scope

The ramifications of my tracheostomy tube are evident in that a balloon cuff is located on the inner cannula, unlike current types of tracheostomy tube that have the balloon cuff located on the outer cannula. By analyzing this preferred embodiment, the balloon cuff located on the inner cannula, the reader will see that my tracheostomy tube provides benefits that outweigh the problems associated with current tracheostomy tubes manufactured today. The scope of this concept can be easily understood, when compared to prior art. This and other objects and advantages of my tracheostomy tube, shall become apparent from the description and drawings herein noted and illustrated. Furthermore, my tracheostomy tube has the additional advantages in that It allows the easy removal of a damaged or worn balloon cuff, without having to remove the outer cannula.

It reduces the possibility of irritation, harm, trauma or injury to the stoma site, by eliminating the removal of the outer cannula, whenever the balloon cuff gets damaged, worn or needs to be removed.

It provides the reduction or prevention of the condition know as a tracheal-esophageal fistula, from developing within the trachea into the esophagus.

It allows another alternative and or choice to current tracheostomy tubes being manufactured and used in the medical field today.

In addition, the ability to recognize the need for an airway, to select the most appropriate device and to insert or assist in its insertion is of equal importance. A tracheostomy tube set provides life sustaining and supporting assistance, when a physician surgically inserts an artificial airway into the trachea. Maintenance of inserted artificial airways is also a major responsibility of physicians, nurses, respiratory therapist and or properly trained healthcare practitioners. A tracheostomy tube set can become blocked with mucus and or phlegm, which require removal of an inner cannula, in order to clean and clear or replace it. Airway clearance, including suctioning and assisting with bronchoscopy, is the most common responsibility of nursing and or respiratory care personnel. Proficiency in airway clearance methods requires knowledge of both the indication and complications associated with these procedures. In this role, the practitioner must ensure that the patient's needs are addressed on an individual basis, and that any immediate or long-term risks to the patient are minimized. Last, healthcare practitioners skilled in the art of airways assume an important role in deciding when and how best to remove and artificial airway. It is toward this goal, of restoration of normal airway function that the practitioner must always strive for.

The Z-79 Committee of the American National Standards Institute recommends guidelines for implant testing (IT) for tracheostomy tubes. Z-79 or IT markings on a tracheostomy tube show that it has passed this test. Other markings on tracheostomy tubes may include the manufacturer's name, type of tube, inside diameter and outside diameter in millimeters and length of the tracheostomy tube also in millimeters.

Although the description above contains many specificities, these should not be construed as limiting the scope of the invention but as merely providing illustrations of some of the presently preferred embodiments of my invention. It is therefore obvious that other equivalent types of tracheostomy tubes and similar types of materials are possible. For example, the swivel locking adapter can have other shapes or materials, such as retaining clips, key and hole type joining structures, etc.; the balloon cuff can also be made in different forms, materials or sizes, etc.; the inner or outer cannulas can be made in various materials or sizes for children, adolescents, adults and geriatric patients, etc.; the tracheostomy tube materials can be made out of a laser proof material, so that if laser surgery is being performed near the stoma or upper chest, the tube will not be compromised. From the above description, I have illustrated and described a new and improved tracheostomy tube and have made certain specific indications as to the materials of which the tracheostomy tube unit parts can be made. I once more desire that the above is taken as illustrative and should not be considered limiting to the particular form(s) shown. In ending, as it will be apparent to those skilled in the manufacturing and in previous art, that I have improved my tracheostomy tube in design, which has various advantages over prior tracheostomy tubes. Thus the scope of the invention should be determined by the claims and their legal equivalents, rather than by the examples given.

What is claimed is:

1. A tracheostomy tube assembly comprising:

an uncuffed outer cannula having a distal end opening and proximal end opening;

a removable inflatable cuffed inner cannula, having an inflatable cuff at a distal end opening, said removable cuffed inner cannula for insertion into said uncuffed outer cannula, and extending from said uncuffed outer cannula distal end opening exposing said removable inflatable cuffed inner cannula from said uncuffed outer cannula distal end opening;

an attachment means including a swivel locking adapter bonded to proximal end opening of said removable inflatable cuffed inner cannula;

an attachment means to said uncuffed outer cannula proximal end opening for mating said swivel locking adapter bonded to said proximal end opening of said removable inflatable cuffed inner cannula;

a bonded inner cannula ring on said removable inflatable cuffed inner cannula, above said inflatable cuff on an external side; and an outer cannula ring indentation at said distal end opening of said uncuffed outer cannula for mating with said inner cannula ring on said removable inflatable cuffed inner cannula, thereby providing a means to prevent secretions from traveling upward between the inner and outer cannula's.

2. A tracheostomy tube assembly as set forth in claim 1 further including an outer cannula retainer having distal ends wherein said outer cannula proximal end opening attaches to said outer cannula retainer, and swivel eyelets convoluted on said outer cannula retainer, located on said outer cannula retainer for means of securing said uncuffed outer cannula to the user by means of a strap attached to said outer cannula retainer by means of said swivel eyelets located on said outer cannula retainer proximal end opening.

3. A method of inserting a tracheostomy tube assembly as set forth in claim 1 whereby pressure exerted by the cuffed inner cannula reduces a tracheal-esophageal fistula and/or trauma on the tracheal tissue comprising the steps of:

providing said inflatable cuffed inner cannula composed of a flexible silicone material thereby providing flexibility to said cuffed inner cannula; inserting said flexible silicone inflatable cuffed inner cannula into shorter outer cannula composed of a PVC material, said cuffed inner cannula extending from said outer cannula distal end opening;

inserting said tracheostomy tube assembly into a trachea of a patient, whereby said flexibility of the said silicone inflatable cuffed inner cannula reduces pressure exerted on tracheal tissue surfaces diminishing and/or reducing a condition known as a tracheal-esophageal fistula or arterial fistula from forming on tracheal tissue surface;

verifying placement by a physician of said inner cannula mated to said outer cannula with a lateral tracheal airway x-ray to ensure proper position of the tracheostomy tube assembly.

* * * * *